US00PP31001P2

(12) United States Plant Patent
Olesen

(10) Patent No.: US PP31,001 P2
(45) Date of Patent: Nov. 5, 2019

(54) MINIATURE ROSE PLANT NAMED 'POULPAH089'

(50) Latin Name: *Rosa hybrid*
Varietal Denomination: Poulpah089

(71) Applicant: Mogens Nyegaard Olesen, Fredensborg (DK)

(72) Inventor: Mogens Nyegaard Olesen, Fredensborg (DK)

(73) Assignee: Poulsen Roser A/S, Fredensborg (DK)

( * ) Notice: Subject to any disclaimer, the term of this patent is extended or adjusted under 35 U.S.C. 154(b) by 0 days.

(21) Appl. No.: 15/999,577

(22) Filed: Sep. 4, 2018

(51) Int. Cl.
*A01H 5/02* (2018.01)
*A01H 6/74* (2018.01)

(52) U.S. Cl.
USPC ..... Plt./119
CPC ..... *A01H 6/74* (2018.05); *A01H 5/02* (2013.01)

(58) Field of Classification Search
USPC ..... Plt./119, 120, 118
CPC ..... A01H 5/0222
See application file for complete search history.

(56) References Cited

PUBLICATIONS http://www.helpmefind.com/rose/l.php?I=2.81782.0; No Date; 1 page.*

* cited by examiner

*Primary Examiner* — Kent L Bell

(57) ABSTRACT

A new garden rose plant of the Miniature class which has abundant, orange flowers and attractive foliage. This new and distinct variety has shown to be uniform and stable in the resulting generations from asexual propagation.

2 Drawing Sheets

Botanical designation: *Rosa* hybrid.
Variety denomination: 'Poulpah089'.

SUMMARY OF THE INVENTION

The present invention constitutes a new and distinct variety of rose plant which originated from a controlled crossing between the female seed parent, an unnamed seedling, and the male pollen parent, also an unnamed seedling. Both of the parent varieties are non-patented.

The two parents were crossed during the summer of 2007 and the resulting seeds were planted in a controlled environment in Fredensborg, Denmark. The new variety, named 'Poulpah089', originated as a single seedling from the stated cross.

The new variety may be distinguished from its male pollen parent and female seed parent primarily by the following characteristics. The male pollen parent plant has yellow flowers while the new variety has orange flowers. The female seed parent plant has light apricot flowers while the new variety has orange flowers.

The objective of the hybridization of this rose variety was to create a new and distinct variety with unique qualities, such as:

1. Uniform and abundant orange flowers;
2. Vigorous, but compact growth when propagated on its own roots;
3. Exceptional disease resistance.

This combination of qualities is not present in previously available commercial cultivars of this type, known to the inventor, and distinguish 'Poulpah089' from all other varieties of which we are aware.

As part of the rose development program, Mogens N. Olesen germinated the seeds from the aforementioned hybridization during winter of 2007 and conducted evaluations on the resulting seedlings in a controlled environment in Fredensborg, Denmark. 'Poulpah089' was selected in the spring of 2008 by the inventor as a single plant from the progeny of the aforementioned hybridization.

Asexual reproduction of 'Poulpah089' by rooted cuttings was first done by Mogens N. Olesen in the nursery in Fredensborg, Denmark in July, 2008. This initial and other subsequent asexual propagations conducted in controlled environments have demonstrated that the characteristics of 'Poulpah089' are true to type and are transmitted from one generation to the next.

DESCRIPTION OF THE DRAWING

The accompanying color illustrations show as true as is reasonably possible to obtain in color photographs of this type, the typical characteristics of the buds, flowers, leaves, and stems, of 'Poulpah089'.

Specifically illustrated in FIG. 1 of the drawings are open flower viewed from above, a flower cluster on a branch, flower petals detached, and sepals detached showing reproductive flower parts.

Figure 1:
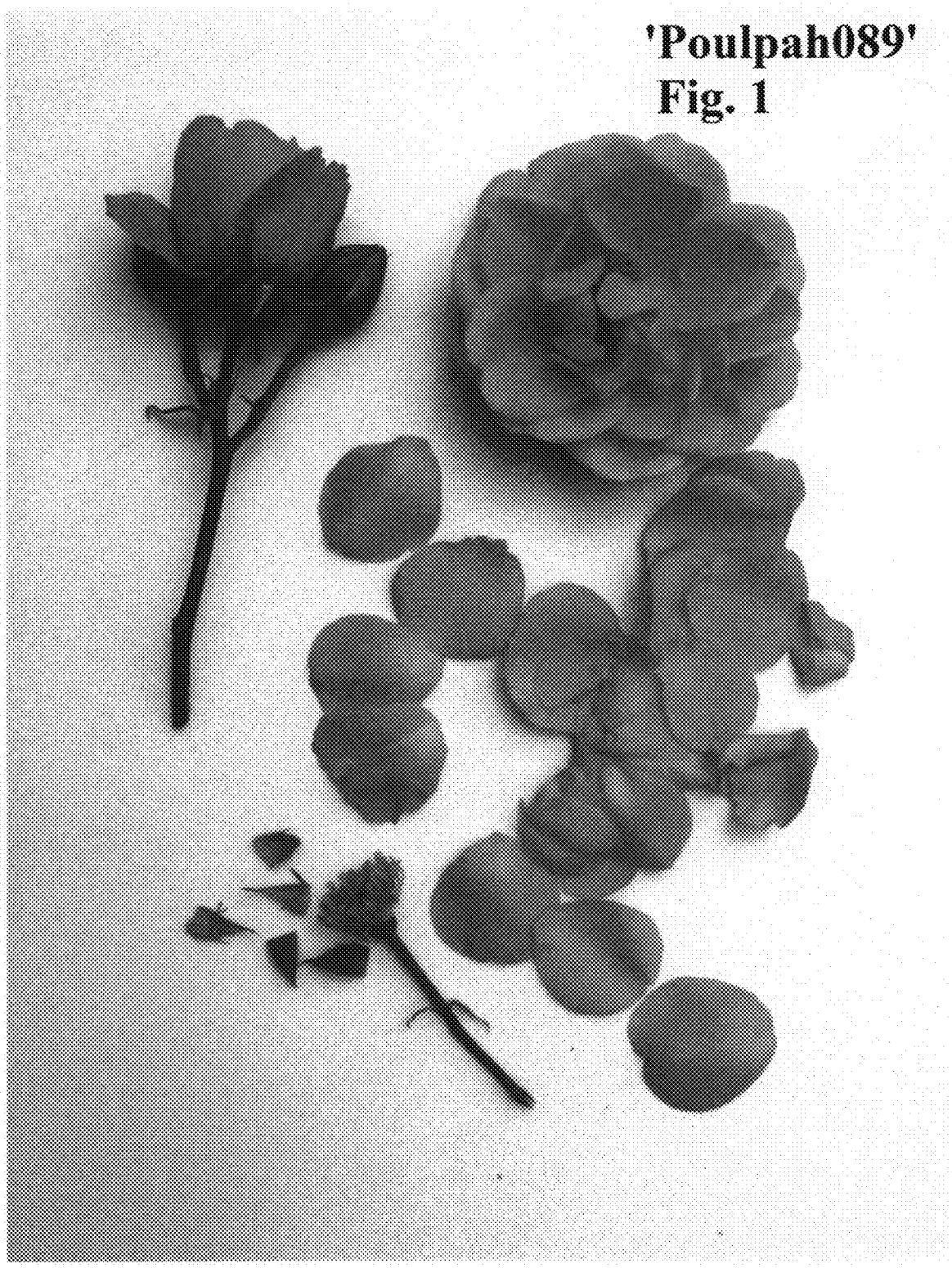
Figure 2:
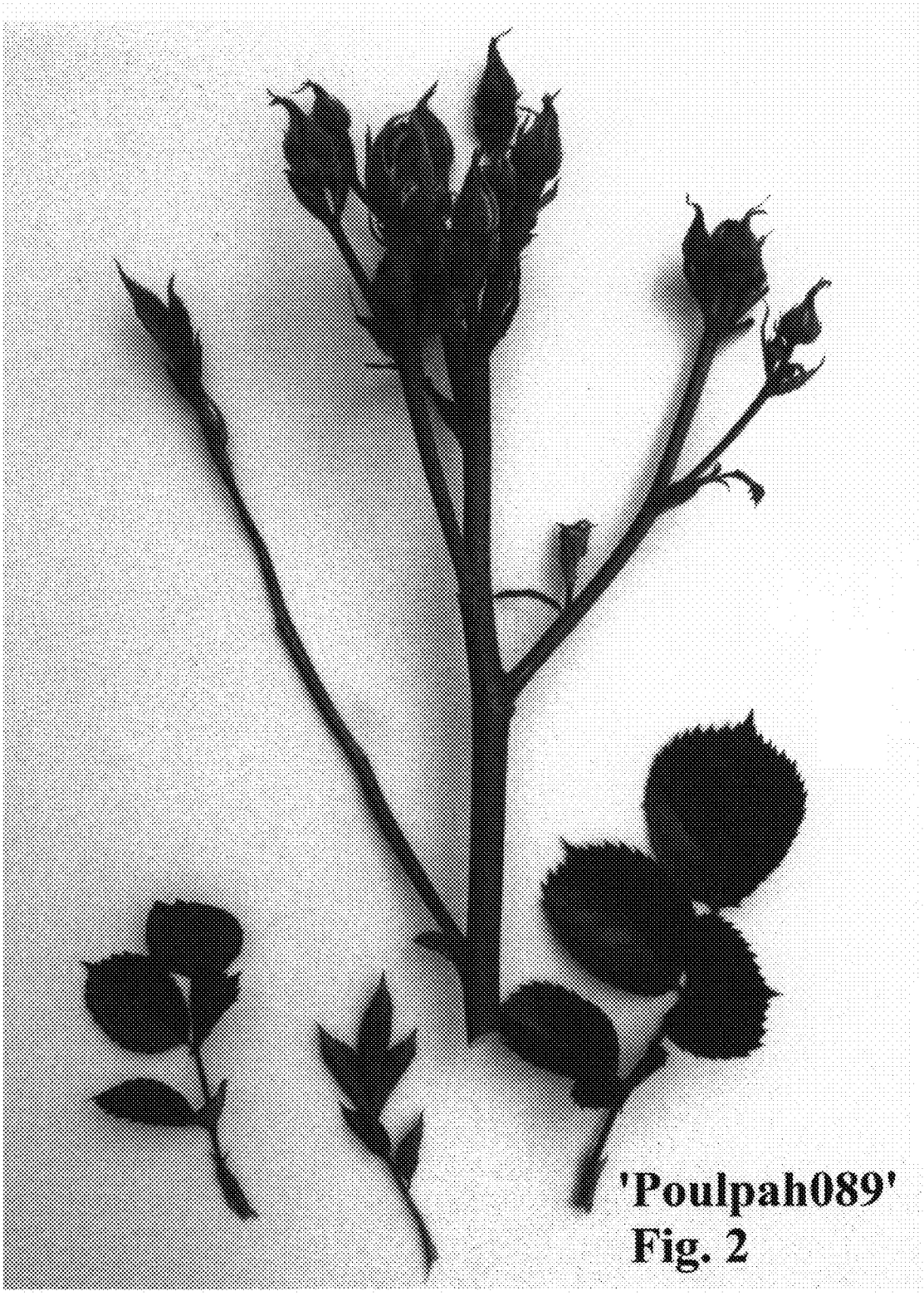

Specifically illustrated in FIG. 2 of the drawings are leaves and a flowering branch with flower buds. Plants shown are 2 years of age.

DETAILED DESCRIPTION OF THE VARIETY

The following is a description of 'Poulpah089',as observed in its growth in a field nursery in Marion County, Oreg. Observed plants are 2 years of age, and were grown on their own roots. Color references are made using The Royal Horticultural Society (London, England) Colour Chart, 2001, except where common terms of color are used.

For a comparison, several physical characteristics of the rose variety 'Poulpah064', U.S. Plant Pat. No. 25,971 are compared to 'Poulpah089' in Chart 1.

CHART 1

Comparison with 'Poulpah064'

| | 'Poulpah089' | 'Poulpah064' |
|---|---|---|
| Petal Count | 30 | 35 |
| Flower Diameter | 60 to 70 mm | 60 mm |
| General Tonality of Flower Color | Yellow-Orange Group 23C and Orange Group 25C. | Yellow-Orange Group 14C with intonations of Yellow-Orange Group 22B |

FLOWER AND FLOWER BUD

Blooming habit: Continuous.

Flower bud:

*Size.*—Upon opening, 19 mm in length from base of receptacle to end of bud. Bud diameter is 13 mm.

*Bud form.*—Ovoid.

*Bud color.*—As sepals divide petals are Red Group 53A, Yellow Group 12B, and Orange-Red Group 24A.

*Sepal inner surface.*—Color: Yellow-Green Group 138C. Surface: Lightly pubescent.

*Sepal outer surface.*—Color: Yellow-Green Group 144A, with intonations of Greyed-Purple Group 183B. Texture: Smooth.

*Sepal shape.*—Apex: Cirrhose. Base: Flat at union with receptacle.

*Sepal margin.*—Margins have moderate foliaceous appendages on three of the five sepals.

*Sepal size.*—20 mm long, 5 mm wide.

*Receptacle.*—Texture: Smooth. Size: 4 mm in height, 6 mm wide. Color: Yellow-Green Group 144A. Shape: Campanulate.

*Pedicel.*—Surface: Smooth. Length: 20-25 mm. Diameter: 3 mm on average. Color: Yellow-Green Group 144B, with intonations of Greyed-Red Group 180B. Strength: Strong.

*Peduncle.*—Length: 1 to 3 cm. Diameter: About 3 mm. Color: Greyed-Red Group 180A with Yellow-Green Group 144A. Texture: Smooth.

Flower bud development: Flower buds are borne in clusters of 5 to 8 flower buds per stem.

Flower bloom:

*Fragrance.*—Moderate.

*Duration.*—The blooms have a duration on the plant of approximately 10 days. Petals fall cleanly away from plant after flowers have fully matured.

*Size.*—Flower diameter is 60 to 70 mm when open. Flower depth is 25 mm.

*Flower shape.*—Open cup double flower, with petals that curve out from the center.

*Shape of flower, side view.*—The upper portion is a flattened convex. The lower portion is flat.

Petalage: Under normal conditions, flowers have about 30 petals.

General tonality of flower: Open flowers are Yellow-Orange Group 23C and Orange Group 25C.

Petal color:

*Upon opening, inner and outer petals.*—Upper surface: Yellow-Orange Group 19A. At the base, Yellow Group 14B. Lower surface: Yellow Group 14B at the base, with shades of Yellow-Orange Group 18A and Orange-Red Group 31B.

*After opening, outer and inner petals.*—Upper surface: Yellow-Orange Group 18B at mid section, and Red Group 38A at margins. Basal section is Yellow Group 9A. Lower surface: Yellow-Orange Group 18B and Orange Group 35C. At the base of the petal, Yellow Group 8A.

Petals:

*Petal reflex.*—None.

*Margin.*—Entire and uniform. No undulations.

*Shape.*—Rounded. Apex shape: Rounded. Base shape: Rounded.

*Size.*—32 mm (l)×35 mm (w).

*Texture.*—Smooth.

*Thickness.*—Average.

Petaloids:

*Size.*—20 mm (l) by 7 mm (w).

*Quantity.*—2 to 4.

*Shape.*—Broad based ellipse.

*Color.*—Upper surface is Yellow-Orange Group 19A. At the base, Yellow Group 14B. The lower surface is Yellow Group 14B at the base, with shades of Yellow-Orange Group 18A and Orange-Red Group 31B.

Reproductive flower parts:

*Pollen.*—None observed.

*Anthers.*—Size: 3 mm in length. Color: Yellow Group 14D. Quantity: 65 on average.

*Filaments.*—Color: Yellow Orange Group 14A with intonations of Orange-Red Group 34B. Length: 5 mm.

*Pistils.*—Length; 5 mm. Quantity: 25 on average.

*Stigmas.*—Color: Greyed-Yellow Group 160A.

*Styles.*—Color: Greyed-Yellow Group 160A.

*Location of stigmas.*—Level in location relative to the length of the filaments and the height of the anthers.

*Hips.*—None Observed.

PLANT

Plant growth: Upright, bushy. Plants are 35 cm in height, and 35 cm wide.

Stems:

*Color of juvenile growth.*—Yellow-Green Group 146D, with intonations of Greyed-Red Group 180A.

*Color of mature growth.*—Yellow-Green Group 144A.

*Length.*—Canes are about 8 to 10 cm from the base of the plant to the flowering portion.

*Diameter.*—About 5 mm.

*Internodes.*—On mature canes about 30 mm between nodes.

*Surface texture.*—Young wood: Smooth. Older wood: Smooth.

Prickles: None observed.

Plant foliage:

*Compound leaf.*—115 mm (l)×95 (w).

*Quantity.*—2 or 3 leaves per 10 cm of stem on average.

*Leaf bearing angle to the stem.*—45 degrees.

*Color of juvenile foliage*.—Upper side: Yellow-Green Group 146A with Greyed-Purple Group 183C at the margins. Lower side: Yellow-Green Group 146A with Greyed-Purple Group 183C at the margins.

*Color of mature foliage*.—Upper side: Yellow-Green Group 146A. Lower side: Yellow-Green Group 146C.

Plant leaves and leaflets:

*Stipules*.—Size: 6 mm long, 3 mm wide. Quantity: 2 per compound leaf. Shape: Linear, slightly broad based with outward extending apices. Margins: Finely serrated. Color: Yellow-Green Group 144A.

*Petiole*.—Length: 10 mm. Diameter: 1.5 mm. Upper surface color: Yellow-Green Group 144B, with intonations of Greyed-Purple Group 183A. Lower surface color: Yellow-Green Group 144B.

*Rachis*.—Length: 40 mm Upper surface color: Yellow-Green Group 144B, with intonations of Greyed-Purple Group 183A. Lower surface color: Yellow-Green Group 144B.

*Leaflet*.—Quantity: Normally 5 leaflets. Margins: Serrated. Size: Terminal leaflets are about 50 mm long, 45 mm wide. Shape: Generally elliptical. Base: Rounded. Apex: Mucronate. Texture: Smooth. Thickness: Average. Arrangement: Odd pinnate. Venation: Reticulate. Glossiness: Glossy.

Disease resistance: Above average resistance to powdery mildew *Sphaerotheca pannosa*, downy mildew *Peronospora sparsa*, rust *Phragmidium* sps., black spot *Diplocarpon rosae*, and *Botrytis cinerea* under normal growing conditions.

Cold hardiness: The variety is tolerant to USDA Cold Hardiness Zone 6.

Heat tolerance: The variety has been found to be suitable for climate conditions found in the American Horticulture Society heat zone 7.

I claim:

1. A new and distinct variety of rose plant named 'Poulpah089', substantially as illustrated and described herein, due to its abundant orange flowers, disease resistance, and extended period of bloom.

* * * * *

'Poulpah089'

'Poulpah089'